United States Patent [19]

Mathew et al.

[11] 3,931,331
[45] *Jan. 6, 1976

[54] PROCESS OF PREPARING α-FORMYL SULFIDES AND 2-HYDROCARBYLTHIOALDOXIMES THEREFROM

[75] Inventors: Chempolil Thomas Mathew, Randolph; Harry Edwards Ulmer, Morristown, both of N.J.

[73] Assignee: Allied Chemical Corporation, New York, N.Y.

[ * ] Notice: The portion of the term of this patent subsequent to Mar. 25, 1992, has been disclaimed.

[22] Filed: Oct. 24, 1974

[21] Appl. No.: 517,679

Related U.S. Application Data

[63] Continuation of Ser. No. 327,979, Jan. 30, 1973, Pat. No. 3,873,624.

[52] U.S. Cl...... 260/601 R; 260/465 D; 260/465 E; 260/465 F; 260/465 G; 260/465 H; 260/470; 260/476; 260/479 S; 260/481 R; 260/503; 260/505 R; 260/505 C; 260/507 R; 260/508; 260/509; 260/511; 260/513 R; 260/513 N; 260/514 G; 260/514 H; 260/514 J; 260/516; 260/534 S; 260/563 R; 260/566A; 260/584 A; 260/598; 260/599; 260/601 H; 260/946
[51] Int. Cl.²........................................ C07C 47/00
[58] Field of Search......... 260/465 D, 465 E, 465 F, 260/465 G, 465 H, 468 R, 468 G, 468 H, 470, 476, 479 S, 481 R, 503, 505 R, 505 C, 507 R, 508, 509, 511, 513 R, 513 N, 514 G, 514 H, 514 J, 516, 534 S, 563 R, 584 A, 598, 599, 601 H, 601 R, 946, 566 A

[56] References Cited
OTHER PUBLICATIONS
Wagner et al., "Synthetic Organic Chemistry" pp. 100–101 (1965).

*Primary Examiner*—Gerald A. Schwartz
*Attorney, Agent, or Firm*—Roger H. Criss; Michael S. Jarosz

[57] ABSTRACT

An α-formyl sulfide is prepared by a process which comprises reacting in an aqueous medium an α-haloaldehyde of the formula

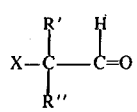

wherein R' and R'' independently are hydrogen, hydrocarbon radicals of 1 to 18 carbon atoms selected from the group consisting of alkyl, cycloalkyl, alkenyl, cycloalkenyl and aryl, or substituted hydrocarbon radicals of the above group, and X is a halogen selected from the group consisting of chlorine, bromine, and iodine, with a thiol salt of the formula R'''SM, wherein R''' is a hydrocarbon radical of 1 to 18 carbon atoms selected from the group consisting of alkyl, cycloalkyl, alkenyl, cycloalkenyl and aryl or a substituted hydrocarbon radical of the above group; and M is an alkali or alkaline earth metal, thereby forming an α-formyl sulfide of the formula

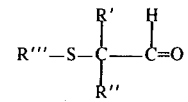

Also, 2-hydrocarbylthioaldoximes are prepared by oximating the above α-sulfides by reaction with a source of hydroxylamine. Additionally, 2-hydrocarbylthioaldoximes are prepared by a process which comprises halogenating an aldehyde having the formula

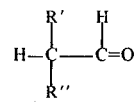

wherein R' and R'' are defined as above, to form an α-haloaldehyde of the formula

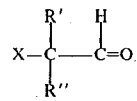

wherein X is defined as above, reacting in an aqueous medium the α-haloaldehyde with a thiol salt of the formula R'''SM, wherein R''' and M are defined as above, to form an α-formyl sulfide of the formula

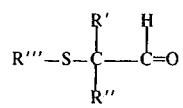

and oximating the α-formyl sulfide to form a 2-hydrocarbylthioaldoxime of the formula

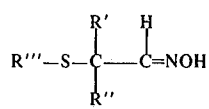

12 Claims, No Drawings

PROCESS OF PREPARING α-FORMYL SULFIDES AND 2-HYDROCARBYLTHIOALDOXIMES THEREFROM

This is a continuation, of Application Ser. No. 327,979, filed Jan. 30, 1973.

BACKGROUND OF THE INVENTION

1. Field of the Invention

This invention relates to a process for preparing α-formyl sulfides and 2-hydrocarbylthioaldoximes therefrom.

2. Description of the Prior Art

A process for the preparation of 2-hydrocarbylthioaldoxime compounds has been suggested by U.S. Pat. No. 3,217,036 (issued 1965 to Payne). An example of such compounds is 2-methyl-2-methylthiopropionaldoxime, which is useful as a nematocide as well as for preparing 2-methyl-2-methylthiopropionaldehyde-N-methylcarbamoyloxime which is useful as a pesticide. It is suggested in the said United States patent to prepare the 2-methylthioaldoxime by reacting in an organic solvent methylmercaptan in the presence of a base with the azodioxy-coupled dimer of 1-nitroso-2-chloro-2-methylpropane. The dimer may be prepared by the reaction of isobutylene with nitrosyl chloride or the combination of sodium nitrite and hydrochloric acid.

The process of Payne has its drawbacks in that the dimer is unstable (explosive) at elevated temperatures and the reported yields have been relatively low.

It has also been suggested by Kirrmann et al., (Chemical Abstracts 61:8180a) to react in anhydrous ether certain α-chloroaldehydes, including α-chloroisobutyraldehyde, with sodium thiomethylate to give α-(methylthio)aldehyde, but in yields in the range of 55 to 80%. Besides the low yields, the necessity for carrying out the reaction in anhydrous ether requires a costly purification or wastage of the solvent.

It has been additionally suggested in U.S. Pat. No. 3,419,617 (issued 1968 to Doss) to form α-formyl sulfides by reacting α-haloaldehydes with a thiol in the presence of pyridine and derivatives thereof. The suggested process also has its drawbacks as pyridine and its derivatives are normally too impure following reaction to recycle, thereby increasing processing costs. Doss discloses that the desired reaction does not occur in the presence of water.

SUMMARY OF THE INVENTION

In accordance with one embodiment of this invention, an α-formyl sulfide is prepared by a process which comprises reacting in an aqueous medium and α-haloaldehyde of the formula

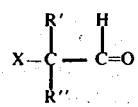

wherein R' and R'' independently are hydrogen, hydrocarbon radicals of 1 to 18 carbon atoms selected from the group consisting of alkyl, cycloalkyl, alkenyl, cycloalkenyl and aryl or substituted hydrocarbon radicals of the above group, and X is a halogen selected from the group consisting of chlorine, bromine and iodine, with a thiol salt of the formula R'''SM, wherein R''' is a hydrocarbon radical of 1 to 18 carbon atoms selected from the group consisting of alkyl, cycloalkyl, alkenyl, cycloalkenyl and aryl or a substituted hydrocarbon radical of the above group; and M is an alkali or alkaline earth metal, thereby forming an α-formyl sulfide of the formula

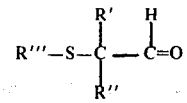

When R' and R'' is a substituted hydrocarbon radical of the above defined group, the substituted moiety may be selected from the group consisting of alkyl of 1 to 18 carbon atoms, aryl of 6 to 18 carbon atoms, halogen, cyano, sulfo, mercapto, alkylthio of 1 to 6 carbon atoms, hydroxy, alkoxy of 1 to 6 carbon atoms, dialkoxy phosphino in which each alkoxy group contains 1 to 6 carbon atoms, dialkyl phosphonoxy in which each alkyl group contains 1 to 6 carbon atoms, carboxy, alkoxy carbonyl in which the alkoxy group contains 1 to 6 carbon atoms, nitro and combinations thereof. When R''' is a substituted hydrocarbon radical of the above defined group, the substituted moiety may be selected from the group consisting of alkyl of 1 to 18 carbon atoms, aryl of 6 to 18 carbon atoms, halogen, cyano, alkylthio of 1 to 6 carbon atoms, amino, alkylamino and dialkylamino of 1 to 6 carbon atoms in each alkyl group, amido, sulfo, sulfonamido, hydroxy, alkoxy of 1 to 6 carbon atoms, dialkoxy phosphino in which each alkoxy group contains 1 to 6 carbon atoms, dialkyl phosphonoxy in which each alkyl group contains 1 to 6 carbon atoms, carboxy, alkoxy carbonyl in which the alkoxy group contains 1 to 6 carbon atoms, nitro and combinations thereof.

In accordance with another embodiment of this invention, 2-hydrocarbylthioaldoximes are prepared by oximating the above α-formyl sulfides.

In accordance with a further embodiment of this invention, 2-hydrocarbylthioaldoximes are prepared by a process which comprises halogenating with a halogen selected from the group consisting of chlorine, bromine and iodine, an aldehyde having the formula

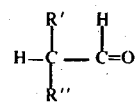

wherein R' and R'' are as defined as above, thereby forming an α-haloaldehyde of the formula

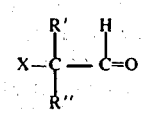

wherein X is defined as above, reacting in an aqueous medium the α-haloaldehyde with a thiol salt of the formula R'''SM, wherein R''' and M are defined as above, thereby forming an α-formyl sulfide of the formula

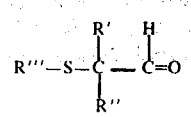

and oximating the α-formyl sulfide, thereby forming a 2-hydrocarbylthioaldoxime of the formula

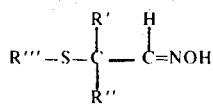

Description of the Preferred Embodiment

In accordance with one preferred embodiment of this invention, an α-formyl sulfide is prepared by reacting in an aqueous medium an α-haloaldehyde of the formula

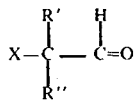

wherein R', R" and X are defined as above, with a thiol salt of the formula R'''SM, wherein R''' and M are defined as above. The reaction may be represented as follows:

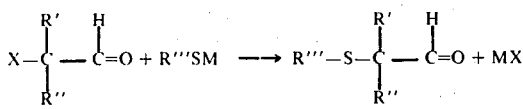

By carrying out the reaction in an aqueous medium, it has been found that it is possible to obtain yields of the α-formyl sulfide on the order of about 85 to 100 percent of the theoretical yield. Such result is surprising since it has been previously reported by Kirrmann et al. that such reaction under anhydrous conditions provides yields only in the order of 55 to 80% and by Doss that a similar reaction between an α-haloaldehyde and a thiol does not occur in the presence of water. By utilizing an aqueous reaction medium, the reaction proceeds more economically since solvent recovery operations can be eliminated.

Any α-haloaldehyde satisfying the above formula can be employed in the reaction of this invention. Preferably, R' and R" are hydrogen or hydrocarbon radicals, as defined previously, of 1 to 6 carbon atoms, more preferably, R' and R" are hydrogen or alkyl of 1 to 4 carbon atoms. Examples of such α-haloaldehydes are chloroacetaldehyde, bromoacetaldehyde, 2-chloropropionaldehyde, 2-chloroisobutyraldehyde, 2-bromoisobutyraldehyde, 2-chloro-2-methylbutyraldehyde, 2-iodo-n-pentanal, 2-(m-cyanophenyl)-2-chloropropionaldehyde, 2-cyclohexyl-2-chlorohexanal, 2-(2'-cyclohexenyl)-2-bromopropionaldehyde, cyclohexyl-bromoacetaldehyde, 2-allyl-2-bromopropionaldehyde, 2-(2'-cyanoethyl)-2-bromopropionaldehyde, 2-methylthiomethyl-2-chlorobutyraldehyde, 2-(p-methylsulfonamido)-2-bromopropionaldehyde, 2-(3'-nitropropyl)-2-cyclohexyl-2-chloroacetaldehyde, 2-(2'-carbomethoxyethyl)-isopropyl-2-iodoacetaldehyde, 2-(2'-diethoxyphosphinoethyl)-2-chlorobutyraldehyde, 2-(p-carboxyphenyl)methyl-2-chloropropionaldehyde, 2-(o-sulfophenyl)-2-bromopentanal, 2-(2'-dimethylphosphonoxyethyl)-2-chloropropionaldehyde, 2-(m-nitrophenyl)-2-chloroacetaldehyde, and the like. A preferred class of compounds are α-haloaldehydes of the above formula wherein R' and R" are the same or different alkyl radicals of 1 to 4 carbon atoms, such as 2-chloroisobutyraldehyde, 2-bromoisobutyraldehyde, etc.

The above α-haloaldehydes can be prepared by conventional methods. For example, 2-chloroisobutyraldehyde may be prepared by the reaction of chlorine and isobutyraldehyde. Such reaction is preferably carried out under reflux conditions by admitting chlorine gas and liquid isobutyraldehyde into a reactor with the gas preferably admitted above the surface of the isobutyraldehyde. Alternately, other conventional methods may be utilized for the chlorination or other halogenation reaction. It has been found that chlorination of isobutyraldehyde under reflux conditions minimizes the formation of oligomers of α-chloroisobutyraldehyde, which oligomers generally should be avoided as is further explained below. Reaction temperatures of between about 50° to 120°C. may be utilized in the preparation of α-chloroisobutyraldehyde with the preferred temperature being in the range of about 65° to 90°C. Stoichiometric amounts of reactants are preferably employed, although it may be desired to use an excess of the aldehyde in some instances. Large excess amounts of chlorine should be avoided in order to minimize formation of dichloro and other multi-chloro substituted aldehydes, which, of course, reduce the yield of the mono-chloro aldehydes.

As indicated above, the formation of oligomers of α-chloroisobutyraldehyde can be minimized by reacting chlorine gas and isobutyraldehyde under reflux conditions. Such oligomers, which are predominantly the trimer, have been produced by previously suggested methods of chlorinating with chlorine gas in the neat at other than reflux temperatures or in the presence of aqueous hydrochloric acid. Also, other undesirable products may be formed, such as isobutyric acid when the reaction is carried out in water. Furthermore, it is preferred to minimize the presence of such oligomers in order to increase the yield of the corresponding oxime produced from the α-formyl sulfide.

In order to avoid oligomer formation subsequent to the formation of the monomeric α-chloroisobutyraldehyde, freshly prepared α-chloroisobutyraldehyde may be directly distilled into a reaction vessel for reaction with the thiol salt, or, alternatively, the α-chloroisobutyraldehyde may be maintained at elevated temperatures (e.g. about 40° to 90°C., preferably 50° to 65°C.) before it is reacted with the thiol salt.

Generally, any thiol salt satisfying the formula R"'SM, as defined above, can be employed in this invention. As described above, M is an alkali or alkaline earth metal, such as sodium, lithium, potassium, calcium, barium, and the like. Examples of such thiol salts are the sodium and other alkali and alkaline earth metal salts of methanethiol, ethanethiol, 2-butanethiol, isobutanethiol, 1-dodecanethiol, benzenethiol, p-toluenethiol, 2-cyanoethanethiol, 2-hydroxyethanethiol, p-chlorobenzenethiol, 2-propene-1-thiol, cyclohexanethiol, 3-methoxypropanethiol, 2-cyclohexenethiol, p-dimethylaminobenzenethiol, 2-(dimethylphosphonoxy)ethanethiol, 3-amidopropane-1-thiol, p-nitrobenzenethiol, m-sulfobenzenethiol, 2(2'-hydroxyethoxy)ethanethiol, p-(dimethylphosphonoxy)benzenethiol, 4-aminobutane-1-thiol, and the like.

The above thiol salts can be prepared by any conventional method. Sodium thiomethylate may be prepared, for example, by the reaction of methylmercaptan with sodium hydroxide by bubbling methylmercaptan into an aqueous solution of sodium hydroxide, preferably containing 20 to 25 percent by weight solute. Concentrations above 25 percent should be avoided as they tend to form precipitates whereas concentrations below 20 percent are too dilute for practical purposes. However, concentrations outside of the preferred ranges can also be used, if desired.

As discussed below, a preferred α-formyl sulfide is 2-methyl-2-methylthiopropionaldehyde which can be formed by the reaction of 2-chloroisobutyraldehyde and sodium thiomethylate. Such reaction is preferably conducted under basic conditions to neutralize any hydrochloric acid present along with the aldehyde; this can be provided by utilizing excess sodium hydroxide (for example, about 1 to 10 mol percent excess) in the preparation of the sodium thiomethylate employed in the reaction.

Preferably, the reaction between the α-haloaldehyde and the thiol salt is carried out with stoichiometric amounts of reactants, although excess amounts of either reactant, for example, up to 50 mol percent, or more, can be utilized, if desired. As previously mentioned, the reaction is conducted in an aqueous medium. Preferably, the aqueous medium is provided by utilizing the thiol salt in the form of an aqueous solution preferably containing 2 to 70 percent, more preferably 20 to 50 percent by weight solute. The reaction temperature depends on the nature of the reactants but is usually carried out at a temperature in the range of about −20° to 90°C., preferably 0° to 50°C., and more preferably 20° to 35°C. The reaction time depends upon the reactivity of the reactants and the temperature employed and can vary, for example, from about 1 minute to about 24 hours. The thus formed α-formyl sulfide can be separated from the reaction mixture by any conventional separation technique such as layer separation, solvent extraction, centrifugation, filtration and the like.

Examples of α-formyl sulfides that can be prepared in accordance with the process of this invention are methylthioacetaldehyde, ethylthioacetaldehyde, 2-methyl-2-methylthiopropionaldehyde, 2-ethylthiopropionaldehyde, 2-isobutylthiopropionaldehyde, 2-methyl-2-phenylthiopropionaldehyde, 2-methyl-2-benzylthio-n-butyraldehyde, 2-methyl-2-(2′-cyanoethylthio)-propionaldehyde, 2-cyclohexylthiopropionaldehyde, 2-(p-chlorophenyl)-thio-n-pentanal, 2-(m-cyanophenyl)-2-ethylthiopropionaldehyde, 2-cyclohexyl-2-methylthiohexanal, 2-methyl-2-(3′-methoxypropylthio)-butyraldehyde, 2-methyl-2-(2′-hydroxyethylthio)-butyraldehyde, 2-(2′-cyanoethyl)-2-(p-dimethylaminophenylthio)-propionaldehyde, 2-isopropyl-2-(2′-carbomethoxyethyl)-2-(4″-aminobutylthio)acetaldehyde, 2-methylthiomethyl-2-(p-nitrophenylthio)-butyraldehyde, 2-methyl-2-(2′-dimethylphosphonoxyethylthio)-propionaldehyde, 2-(p-carboxyphenyl)methyl-2-(2′-cyclohexenyl)thiopropionaldehyde, 2-methyl-2-allylthiopropionaldehyde, 2-(m-sulfophenylthio)-butyraldehyde, 2-(2′-hydroxyethoxy)ethylthiopropionaldehyde, 2-(3′-amidopropyl)thiopropionaldehyde, 2-methyl-2-(p-dimethylphosphonoxyphenyl)thiopropionaldehyde, 2-cyclohexyl-2-(4′-aminobutyl)thioacetaldehyde, and the like. A preferred α-formyl sulfide is 2-methyl-2-methylthiopropionaldehyde.

When preparing some of the above α-formyl sulfides, it is preferred to carry out the reaction under basic conditions to neutralize any excess acid which may be present in the haloaldehyde in order to suppress undesired side reactions. Basic conditions above a pH of 7.5 are preferred in such cases and more preferably a pH in the range of 12.0 to 13.8 is utilized.

The α-formyl sulfides prepared in accordance with this invention may be converted to the corresponding 2-hydrocarbylthioaldoxime by any conventional oximation reaction. Preferably, the α-formyl sulfide is reacted with hydroxylamine or a hydroxylamine-yielding compound. For example, the reaction product 2-methyl-2-methylthiopropionaldehyde may be oximated by contact with hydroxylamine or a hydroxylamine-yielding compound, preferably at a pH of about 3.5 to 8 and at a temperature of about 50°C. to 100°C. More preferably, the pH is in the range of 5 to 6 and the temperature is in the range of 75° to 85°C. Since hydroxylamine is an unstable compound, the oximation reaction preferably utilizes a hydroxylamine-yielding compound.

As hydroxylamine-yielding compounds there may be employed hydroxylamine salts or mixtures thereof, such as hydroxylamine sulfate, hydroxylamine bisulfate, hydroxylamine hydrochloride, hydroxylamine phosphate, etc., and the oximes, i.e., compounds of the formula

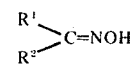

wherein each of $R^1$ and $R^2$ independently represents hydrogen or an alkyl group of 1 to 6 carbon atoms or $R^1$ and $R^2$ together represent a cyclohexyl group. Examples of such oximes include acetoxime, cyclohexanone oxime, acetaldehyde oxime, methylethylketoxime, etc.

It is particularly preferred to utilize an aqueous solution containing hydroxylamine sulfate; this solution may also contain ammonium sulfate and sulfuric acid. With respect to reactant proportions, it is again preferred to utilize approximately stoichiometric proportions, although up to about 50 mol percent excess or higher of either reactant can be used. The oxime reaction product can be separated from the reaction mixture by any conventional separation technique such as layer separation, solvent extraction, centrifugation, filtration, steam distillation and the like.

The oximation reaction with hydroxylamine can be represented by the equation

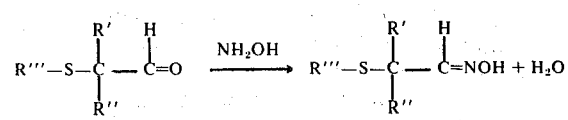

wherein R′, R″ and R‴ are as defined above.

In another embodiment of this invention 2-hydrocarbylthioaldoximes of the formula

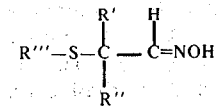

wherein R', R'' and R''' are as defined above, are prepared from aldehydes having the formula

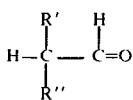

by a process which comprises halogenating the aldehyde with chlorine, bromine or iodine, preferably under reflux conditions, thereby forming an α-haloaldehyde, reacting in an aqueous medium the resultant α-haloaldehyde with a thiol salt of the formula R'''SM, as defined above, thereby forming an α-formyl sulfide and oximating the thus formed α-formyl sulfide.

It has been surprisingly found that the above process provides good overall yields of the 2-hydrocarbylthioaldoxime, for example, in the range of about 50 to 90%. In contrast thereto, when the aldehydes are first oximated and then chlorinated or chlorinated and then oximated prior to thiohydrocarbylation, the desired 2-hydrocarbylthioaldoximes are either not produced or are produced in very low yields. For example, a halogenation reaction following oximation of the aldehyde results in substitution of the halogen atom on the alpha carbon of the oxime, rather than on the 2 carbon as desired. Similarly, if the aldehyde is first halogenated and then is reacted with hydroxylamine, hydrolysis occurs on the alpha carbon of the aldehyde and the oxime is not produced.

In preparing 2-hydrocarbylthioaldoximes from aldehydes as described above, any aldehyde satisfying the formula

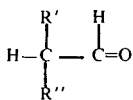

wherein R' and R'' are as defined previously, can be utilized as the starting material. Exemplary aldehydes are the non-halogenated aldehydes corresponding to the α-haloaldehydes previously described. Halogenation of the aldehyde is preferably carried out by reacting the halogen with the aldehyde under reflux conditions in order to maximize yields by minimizing oligomer formation. Preferably stoichiometric amounts of reactants are utilized, although excess amounts, for example up to 50 mol percent or more, of reactants may be employed. However, large excess amounts of the halogen should be avoided to prevent multihalogenation. Reaction temperatures in the range of −20° to 180°C., more preferably 0° to 120°C., may be employed. The α-haloaldehyde product can be recovered by any conventional method, preferably by distillation.

As previously described with respect to chlorination of isobutyraldehyde, it is preferred to distill the resultant α-haloaldehyde directly into a reaction vessel for reaction with the thiol salt or alternatively to store the α-haloaldehyde at an elevated temperature in order to minimize oligomer formation. The reaction between the α-haloaldehyde and the thiol salt is carried out as previously described, as is the oximation of the α-formyl sulfide to yield the desired 2-hydrocarbylthioaldoximes.

The α-formyl sulfides prepared by the process of this invention have utility as intermediates in forming pharmaceutical agents and agricultural chemicals, such as insecticides, fungicides, herbicides, etc. The corresponding aldoximes, in particular, 2-methyl-2-methylthiopropionaldehyde, are useful as nematocides. The 2-methyl-2-methylthiopropionaldehyde is useful as an intermediate in the preparation of 2-methyl-2-methylthiopropionaldehyde-N-methylcarbamoyloxime which is useful as a pesticide.

The following examples illustrate preferred embodiments of this invention.

EXAMPLE 1

Preparation of 2-Methyl-2-Methylthiopropionaldehyde

To 108 grams (1.5 mols) of isobutyraldehyde heated to reflux (65°C.) was added chlorine gas at the rate of 160 ml. per minute. The gas was admitted into the vapor phase above the liquid surface of the isobutyraldehyde. Addition of 1.5 mols of chlorine was completed (as judged by disappearance of isobutyraldehyde by gas chromatography) in 3-½ hours, during which time reflux was maintained by gradually raising the pot temperature to 90°C. The hydrogen chloride by-product was absorbed in cold water. A yield of 67 percent of α-chloroisobutyraldehyde was obtained.

Methylmercaptan gas was dissolved in 190 grams of a 22 percent aqueous solution of sodium hydroxide at 25°–30°C. until saturated. The solution was then mixed with an additional 10 grams of the 22 percent aqueous sodium hydroxide solution to furnish 250 grams of aqueous sodium thiomethylate solution (1.01 mols).

The chlorinated isobutyraldehyde was distilled (pot temperature 90°–140°C.) directly into the sodium thiomethylate solution which was kept stirred and cooled below 30°C. with ice and water. After distillation of the chloroaldehyde was completed, a colorless organic layer of 122 grams of 2-methyl-2-methylthiopropionaldehyde (98.5 percent purity by gas chromatography) was separated from the top. Redistillation at atmospheric pressure (b.p. 140°–141°C.) furnished 120 grams of the pure aldehyde. A yield of 99.5 percent of 2-methyl-2-methylthiopropionaldehyde was obtained. The overall yield for both steps (preparation of the chloroaldehyde and thioaldehyde) was 66.7 percent.

EXAMPLE 2

Preparation of 2-Methyl-2-Methylthiopropionaldoxime

The total yield of the 2-methyl-2-methylthiopropionaldehyde (120 grams) obtained by Example 1 was mixed with 735 grams of 22.8 percent aqueous solution of hydroxylamine sulfate (1.01 mols), which also contained sulfuric acid and ammonium sulfate. Ammonia gas was introduced until the pH increased to 5.5. After heating with stirring for 1-½ hours at 80°C., and subsequent cooling, a colorless oily top layer of 133.5 grams of 2-methyl-2-methylthiopropionaldoxime (99 percent purity by gas chromatography) was isolated. The yield was 99.0 percent of theoretical.

EXAMPLE 3

Following the procedure of Example 1, 2-(m-cyanophenyl)-2-ethylthiopropionaldehyde is prepared by reacting 2-(m-cyanophenyl)-2-chloropropionaldehyde with an aqueous solution of the sodium salt of ethanethiol. Similar yields are obtained.

EXAMPLE 4

Following the procedure of Example 1, 2-isobutylthiopropionaldehyde is prepared by reacting 2-bromopropionaldehyde with an aqueous solution of the sodium salt of isobutanethiol. Similar yields are obtained.

EXAMPLE 5

Following the procedure of Example 1, 2-methyl-2-(3'-methoxypropylthio)-butyraldehyde is prepared by reacting 2-chloro-2-methylbutyraldehyde with an aqueous solution of the sodium salt of 3-methoxypropane thiol. Similar yields are obtained. Following the procedure of Example 2, the resultant thioaldehyde is reacted with an aqueous solution of hydroxylaminesulfate. Similar yields of the corresponding oxime is obtained.

It is to be understood that variations and modifications of the present invention may be made without departing from the scope of the invention. It is also to be understood that the scope of the invention is not to be interpreted as limited to the specific embodiment disclosed herein, but only in accordance with the appended claims when read in light of the foregoing disclosure.

We claim:

1. A process for preparing an α-formyl sulfide comprising
    a. reacting under reflux conditions a halogen selected from the group consisting of chlorine, bromine and iodine with an aldehyde of the formula

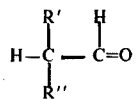

wherein R' and R'' independently are hydrogen, hydrocarbon radicals of 1 to 18 carbon atoms selected from the group consisting of alkyl, cycloalkyl, alkenyl, cycloalkenyl and aryl or substituted hydrocarbon radicals of the above group wherein the substituted moieties are selected from the group consisting of alkyl of 1 to 18 carbon atoms, aryl of 6 to 18 carbon atoms, halogen, cyano, sulfo, mercapto, alkylthio of 1 to 6 carbon atoms, hydroxy, alkoxy of 1 to 6 carbon atoms, dialkoxy phosphino in which each alkoxy group contains 1 to 6 carbon atoms, dialkyl phosphonoxy in which each alkyl group contains 1 to 6 carbon atoms, carboxy, alkoxy carbonyl in which the alkoxy group contains 1 to 6 carbon atoms, nitro and combinations thereof, to thereby form an α-haloaldehyde of the formula

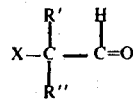

wherein X is chlorine, bromine or iodine, and
    b. reacting in an aqueous medium under basic conditions and at a temperature in the range of about −20 to about 90°C the thus formed α-haloaldehyde with a thiol salt of the formula R'''SM, wherein R''' is a hydrocarbon radical of 1 to 18 carbon atoms selected from the group consisting of alkyl, cycloalkyl, alkenyl, cycloalkenyl and aryl or a substituted hydrocarbon radical of the above group wherein the substituted moiety is selected from the group consisting of alkyl of 1 to 18 carbon atoms, aryl of 6 to 18 carbon atoms, halogen, cyano, alkylthio of 1 to 6 carbon atoms, amido, sulfo, sulfonamido, hydroxy, alkoxy of 1 to 6 carbon atoms, dialkoxy phosphino in which each alkoxy group contains 1 to 6 carbon atoms, dialkyl phosphonoxy in which each alkyl group contains 1 to 6 carbon atoms, carboxy, alkoxy carbonyl in which the alkoxy group contains 1 to 6 carbon atoms, nitro and combinations thereof, and M is an alkali or alkaline earth metal, thereby forming an α-formyl sulfide of the formula

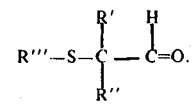

2. The process of claim 1 wherein said α-haloaldehyde formed in step (a) is either directly charged into a reaction vessel wherein step (b) is carried out or is maintained at elevated temperatures prior to step (b) in order to minimize formation of oligomers of said α-haloaldehyde.

3. The process of claim 2 wherein said halogen is chlorine.

4. The process of claim 3 wherein said aldehyde is isobutyraldehyde and wherein the α-chloroisobutyraldehyde formed in step (a) is either directly charged into a reaction vessel wherein step (b) is carried out or is maintained at a temperature in the range of about 40° to 90°C prior to step (b).

5. The process of claim 4 wherein step (a) is conducted at a temperature between about 50° to 120°C.

6. The process of claim 4 wherein said thiol salt is sodium thiomethylate and said α-formyl sulfide is 2-methyl-2-methylpropionaldehyde.

7. The process of claim 6 wherein step (b) is carried out at a pH of 12.0 to 13.8.

8. The process of claim 3 wherein said aldehyde is isobutyraldehyde.

9. The process of claim 8 wherein step (a) is conducted at a temperature between about 50° to 120°C.

10. The process of claim 1 wherein the hydrocarbon radicals representing R' and R'' are alkyl radicals of 1 to 4 carbon atoms.

11. The process of claim 1 including the step of oximating said α-formyl sulfide to form a 2-hydrocarbylthioaldoxime of the formula

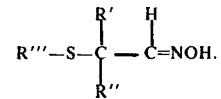

12. The process of claim 6 including oximating the resultant 2-methyl-2-methylthiopropionaldehyde to form 2-methyl-2-methylthiopropionaldoxime.

* * * * *